United States Patent
Tariel

(10) Patent No.: US 9,134,252 B2
(45) Date of Patent: Sep. 15, 2015

(54) HEAD FOR AN EVANESCENT-WAVE FIBRE-OPTIC SENSOR

(75) Inventor: Hugues Tariel, Rennes (FR)

(73) Assignee: DIAFIR, Rennes (FR)

( * ) Notice: Subject to any disclaimer, the term of this patent is extended or adjusted under 35 U.S.C. 154(b) by 0 days.

(21) Appl. No.: 14/235,897

(22) PCT Filed: Jun. 12, 2012

(86) PCT No.: PCT/EP2012/061130
§ 371 (c)(1),
(2), (4) Date: Apr. 28, 2014

(87) PCT Pub. No.: WO2013/017324
PCT Pub. Date: Feb. 7, 2013

(65) Prior Publication Data
US 2014/0233880 A1   Aug. 21, 2014

(30) Foreign Application Priority Data

Jul. 29, 2011 (FR) .................................. 11 56945

(51) Int. Cl.
*G02B 6/00* (2006.01)
*G01N 30/02* (2006.01)
*G01N 30/90* (2006.01)
(Continued)

(52) U.S. Cl.
CPC ........... *G01N 21/8507* (2013.01); *G01J 3/0202* (2013.01); *G01J 3/0218* (2013.01); *G01J 3/42* (2013.01); *G01N 21/552* (2013.01); *G01N 21/3504* (2013.01); *G01N 21/3563* (2013.01);
(Continued)

(58) Field of Classification Search
CPC .................... G01N 21/552; G01N 2021/7783; G01J 3/0218

USPC ........... 385/12; 73/1.22, 1.41, 335.01, 61.48, 73/23.37
See application file for complete search history.

(56) References Cited

U.S. PATENT DOCUMENTS 5,926,269 A * 7/1999 Von Der Eltz et al. ........ 356/300
8,368,899 B2 * 2/2013 Sumetsky ..................... 356/477
(Continued)

FOREIGN PATENT DOCUMENTS

DE          40 38 354          6/1992
WO     WO 2011/121086      10/2011

OTHER PUBLICATIONS

English translation of Written Opinion of the International Searching Authority dated Feb. 24, 2014.
International Search Report for PCT/EP2012/061130 mailed Sep. 14, 2012.
(Continued)

*Primary Examiner* — Robert Tavlykaev
(74) *Attorney, Agent, or Firm* — Nixon & Vanderhye, PC

(57) ABSTRACT

The present invention relates to a head (500) for a sensor comprising two sections of optical fiber enabling the propagation of infrared light having at least one infrared wavelength and generating evanescent waves toward the outside in order to detect infrared signatures of an external medium, said head (500) comprising:
an optical fiber forming a curved portion (15) for connecting the two sections of fiber, and for coming into contact with the external medium so as to detect the infrared signatures interfering with the propagation of the evanescent waves propagating along the fiber, and
means (504, 506) for protecting the curved portion (15) against external mechanical stress, while ensuring that a contact area (30) exists between the external medium and said curved portion (15).

6 Claims, 5 Drawing Sheets

(51) Int. Cl.
  *G01N 21/85* (2006.01)
  *G01J 3/02* (2006.01)
  *G01J 3/42* (2006.01)
  *G01N 21/552* (2014.01)
  *G01N 21/3577* (2014.01)
  *G01N 21/3504* (2014.01)
  *G01N 21/3563* (2014.01)

(52) U.S. Cl.
  CPC .... *G01N 21/3577* (2013.01); *G01N 2021/8528* (2013.01)

(56) References Cited

U.S. PATENT DOCUMENTS

| | | | |
|---|---|---|---|
| 2003/0185483 A1* | 10/2003 | Bennett et al. | 385/14 |
| 2004/0076377 A1* | 4/2004 | Mizukami et al. | 385/77 |
| 2004/0118997 A1 | 6/2004 | Lehmann et al. | |
| 2008/0204708 A1* | 8/2008 | Shaw | 356/36 |
| 2010/0061681 A1* | 3/2010 | Powell | 385/56 |

OTHER PUBLICATIONS

Written Opinion of the International Searching Authority mailed Sep. 14, 2012 (foreign language).

* cited by examiner

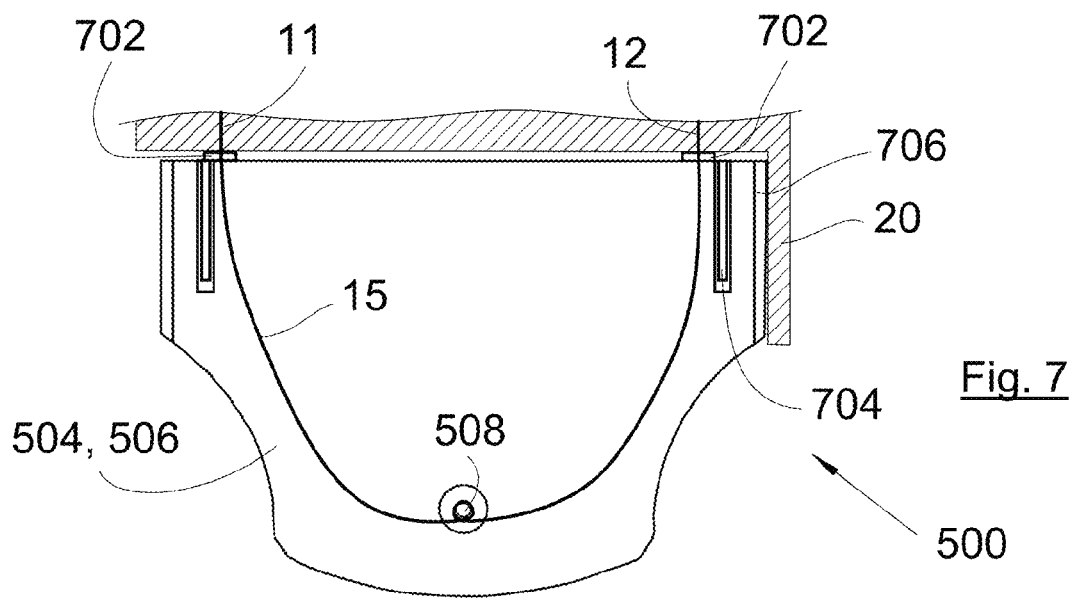
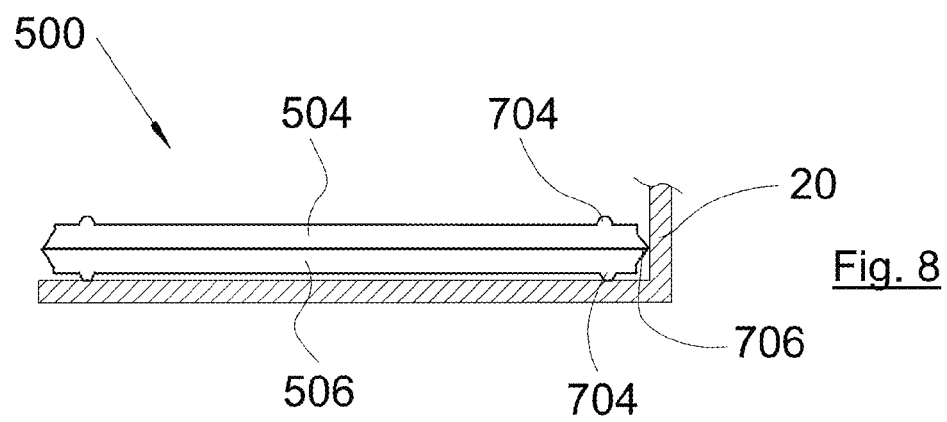

HEAD FOR AN EVANESCENT-WAVE FIBRE-OPTIC SENSOR

This application is the U.S. national phase of International Application No. PCT/EP2012/061130 filed 12 Jun. 2012 which designated the U.S. and claims priority to FR 11/56945 filed 29 Jul. 2011, the entire contents of each of which are hereby incorporated by reference.

The present invention concerns a head for a sensor comprising an optical fibre enabling infrared light to be propagated at at least one infrared wavelength and generating evanescent waves to the outside in order to detect infrared signatures of an external medium. The present invention also concerns a sensor having such a head and a spectrometry system using such a sensor.

The development, in the past years, of optical fibres has enabled the development of sensors used for implementing a special infrared spectrometry technique the originality of which is related to the existence of an evanescent wave that runs over the external surface of the fibre when the latter has an infrared light flow passing through it. The principle of these sensors is to emit an infrared wave in the optical fibre. This wave propagates inside and along the fibre; when an external medium is put in contact with this fibre, the propagation of the wave is then interfered with so that certain wavelengths of the wave are absorbed by the external medium. It then suffices to compare the infrared spectrum of the wave emitted with that of the wave received in order to deduce which are the wavelengths that have been absorbed and therefore which are the substances that are contained in the external medium.

In the prior art, this technique is known by the term FEWS (Fibre Evanescent Wave Spectrometry). This technique has the advantage of offsetting the infrared signal of the spectrometer to the analysis site rather than the converse, enabling, firstly, in-situ analyses in real time and, secondly, avoiding falsifying the results by the taking of samples.

The FEWS technique can be used in various fields such as medical or food in order to analyse chemical or biological substances in a liquid, solid or gaseous medium that is external to the fibre.

FIG. 1 shows an example of an evanescent-wave fibre-optic sensor 10 conventionally used for implementing the FEWS technique.

The sensor 10 comprises one (or even more) evanescent-wave optical fibre. Hereinafter, it will be considered that the sensor has only one without for all that limiting the scope of the present invention.

The sensor 10 has a protective sheath 24, a connector 20 and a head 22.

The protective sheath 24 has the optical fibre running through it, which comprises two sections 11 and 12 of fibre, the function of which is to guide an infrared wave from an emitting point to a receiving point and a curved part 15 that connects the two fibre sections 11 and 12.

The curved part 15 is mounted on the head 22 and may be in various forms. It may, for example, be in the form of an elbow or meanders, or be in the form of any winding having one or more turns. FIG. 1 shows highly schematically that the curved part 15 is in the form of a winding comprising several turns.

This curved part 15 can be disconnected from the two sections 11 and 12 at the connector 20. The head 22 comprises a part of the connector 20 that is adapted to plug onto the other part of the connector 20 then present on the protective sheath 24 of the sensor 10. The head 22 of the sensor 10 can then easily be replaced in the event, for example, of damage to this part during use of the sensor 10.

The two sections of fibre 11 and 12 are thus housed in the protective sheath 24 while the curved part 15 at least partially projects beyond the protective sheath 24. This curved part 15 is then intended to come into contact with the external medium in order to detect the infrared signatures interfering with the propagation of the evanescent waves propagating along the fibre.

An evanescent-wave optical fibre can be manufactured from various materials, in particular glasses, which offer a spectral window in the infrared domain, in particular in the medium infrared that extends approximately from 40 to 5000 $cm^{-1}$, or far infrared that ranges approximately from 10 to 400 $cm^{-1}$. This evanescent-wave optical fibre has a diameter of a few hundreds or even a few tens of micrometres. This diameter is not necessarily constant along the fibre and some parts of the fibre may have a smaller diameter, in particular at the curved part 15.

Chalcogenide glasses are one of the materials used for manufacturing such optical fibres. One of the advantages of these glasses, based in particular on sulphur, selenium and/or tellurium, is that they allow light to pass over a wide range of wavelengths in the infrared, which is not the case, for example, with conventional oxide glasses. In addition, the vitreous nature of the material makes it possible to form it in order to manufacture optical fibres. Finally, the nature of the chemical bonds of this material makes it hydrophobic, which is advantageous when it is used as a sensor in water-rich media such as biological samples.

However, evanescent-wave fibre-optic sensors have the drawback of using a glass optical fibre with a relatively small diameter.

Since the sensitive part of the sensor has to come into direct contact with the medium studied, the latter must therefore be left bare and exposed to the external elements. The curved part 15 is therefore subject to breaking because of the relative fragility of the material used and the small diameter of these fibres. The current solution is then to replace the curved part 15 in the event of damage, which involves a long-term maintenance cost for these sensors that is high.

The problem solved by the present invention is proposing a head that increases the mechanical strength of the curved part 15 of the optical fibre of an evanescent-wave fibre-optic sensor.

To this end, the present invention proposes a head for a sensor comprising two sections of optical fibre for propagating infrared light at at least one infrared wavelength and generating evanescent waves toward the outside in order to detect infrared signatures of an external medium, said head comprising:

an optical fibre forming a curved part intended to connect the two sections of fibre and to come into contact with the external medium in order to detect the infrared signature interfering with the propagation of the evanescent waves propagating along the fibre, and means intended to protect the curved part against external mechanical stress, while guaranteeing a contact area between the external medium and said curved part.

According to a first embodiment, when the external medium is solid, the head also comprises means intended to apply a force from said curved part onto said external medium at the contact area.

Advantageously, the curved part of the fibre comprises a turn and the means for applying a force are a spindle slid in this turn.

Advantageously, the radius of curvature of the spindle is 10% less than that of the turn and the radius of curvature of the spindle is designed to prevent any shearing of the fibre.

Advantageously, the means for protecting the curved part consisting of a clevis through which said spindle is disposed.

According to a second embodiment, when the external medium is liquid, the means intended to protect the curved part consist of a first plate and a second plate between which said curved part is placed, said first plate comprising a flow conduit intended to allow the flow of the liquid external medium between the plates.

Advantageously, said second plate comprises a stud and the curved part of the fibre comprises a turn wound around the stud.

Advantageously, said stud is situated facing the opening of the flow conduit.

Advantageously, each plate has two protrusions, each being designed to come opposite a protrusion on the other plate, and between each pair of protrusions an end of the curved part is housed.

According to a variant, at least one plate comprises ribs that can be machined to form support surfaces in two different directions.

According to another variant, each pair of protrusions comprises a rib and a plane that can be machined to form support surfaces in two different directions.

The invention also proposes a sensor comprising:
a protective sheath enclosing two sections of optical fibre enabling infrared light to be propagated at at least one infrared wavelength and generating evanescent waves towards the outside in order to detect infrared signatures of an external medium,
a head according to one of the previous embodiments, and
a connector fixing the head to the protective sheath.

The invention also proposes a spectrometry system comprising a sensor according to the previous embodiment.

The features of the invention mentioned above, as well as others, will emerge more clearly from a reading of the following descriptions of an example embodiment, said description being given in relation to the accompanying drawings, among which:

FIGS. 7 and 8 show the layout details of a head for a sensor according to the invention.

Figure 1:
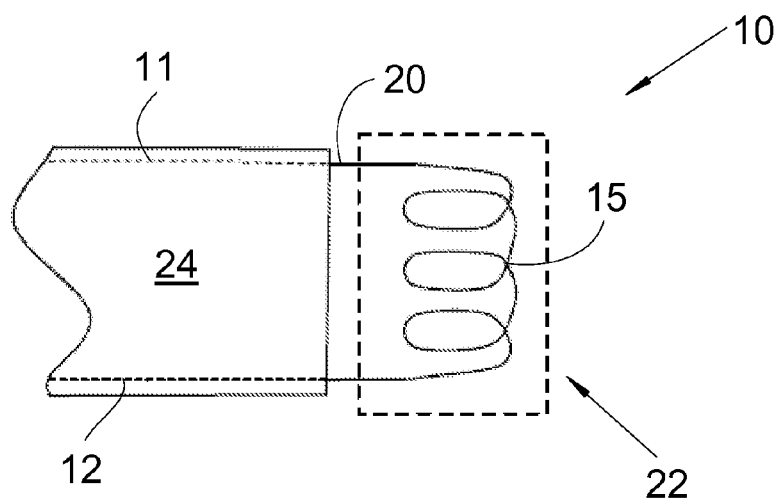
FIG. 1 shows an example of an evanescent-wave fibre-optic sensor.
Figure 2:
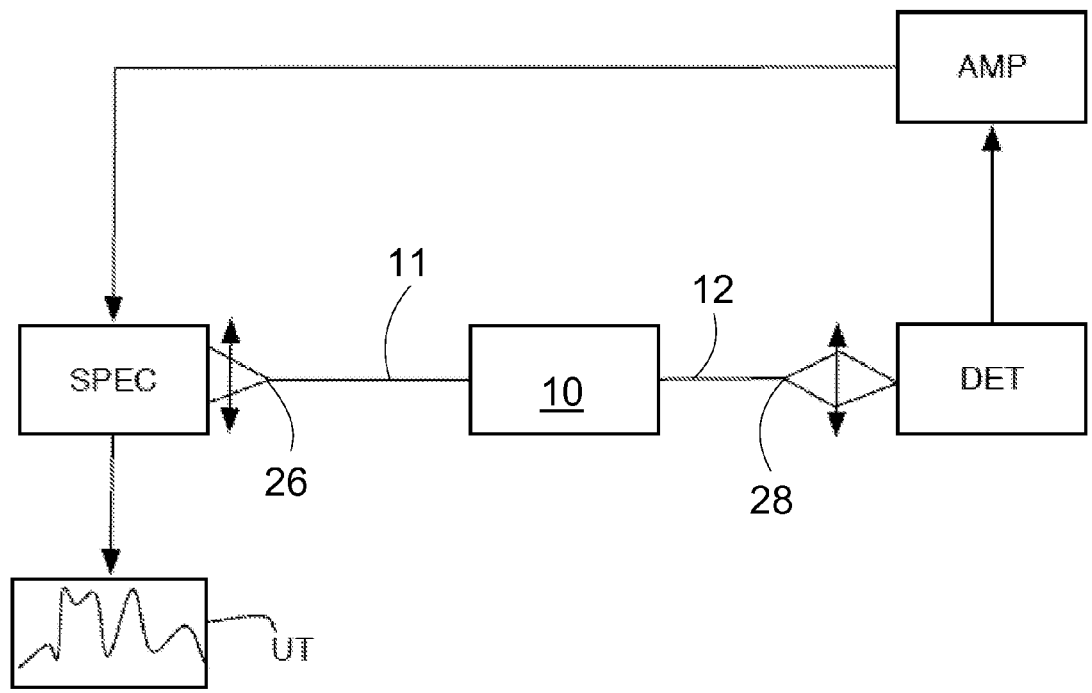
FIG. 2 shows schematically an offset spectrometry system using an evanescent-wave optical fibre.

The system of FIG. 2 is intended to implement an FEWS technique as described in the introductory part. This system comprises a sensor 10 comprising an evanescent-wave optical fibre as described in relation to FIG. 1. In particular, this sensor 10 comprises at least one optical fibre for propagating infrared light at at least one infrared wavelength and generating evanescent waves to the outside in order to detect infrared signatures of an external medium. The fibre comprises over its length two sections of fibre 11 and 12 for guiding an infrared wave, and a curved part 15 that connects the two fibre sections. This curved part 15 is intended to come into contact with the external medium in order to detect the infrared signatures interfering with the propagation of the evanescent waves propagating along the fibre. To this end, the curved part 15 is for example immersed in a test piece containing a sample of a liquid to be analysed.

The system also comprises a spectrometer SPEC connected to a first end 26 of the optical fibre of the sensor 10 via a concentrator in order to emit an infrared wavelength signal.

The second end 28 of the optical fibre of the sensor 10 is connected to an infrared detector DET via a concentrator in order to receive the infrared signal emitted from the first end 26 to this second end 28 via the sections 11 and 12 and the curved part 15. The detector DET is connected to an amplifier AMP for the signal received by the detector DET. The amplified signal is then sent to the spectrometer SPEC, which comprises (or is in relationship with) a signal processing unit UT for comparing the spectrum of the infrared signal received at the second end 28 with the spectrum of the infrared signal emitted at the first end 26. This comparison makes it possible to evaluate the interference contributed by the sample or more generally by the external medium on the curved part 15 of the sensor 10.

In the context of the invention, the spectrometry system is implemented with a sensor 100 according to the invention as described below, that is to say having a special head.

Figure 3:
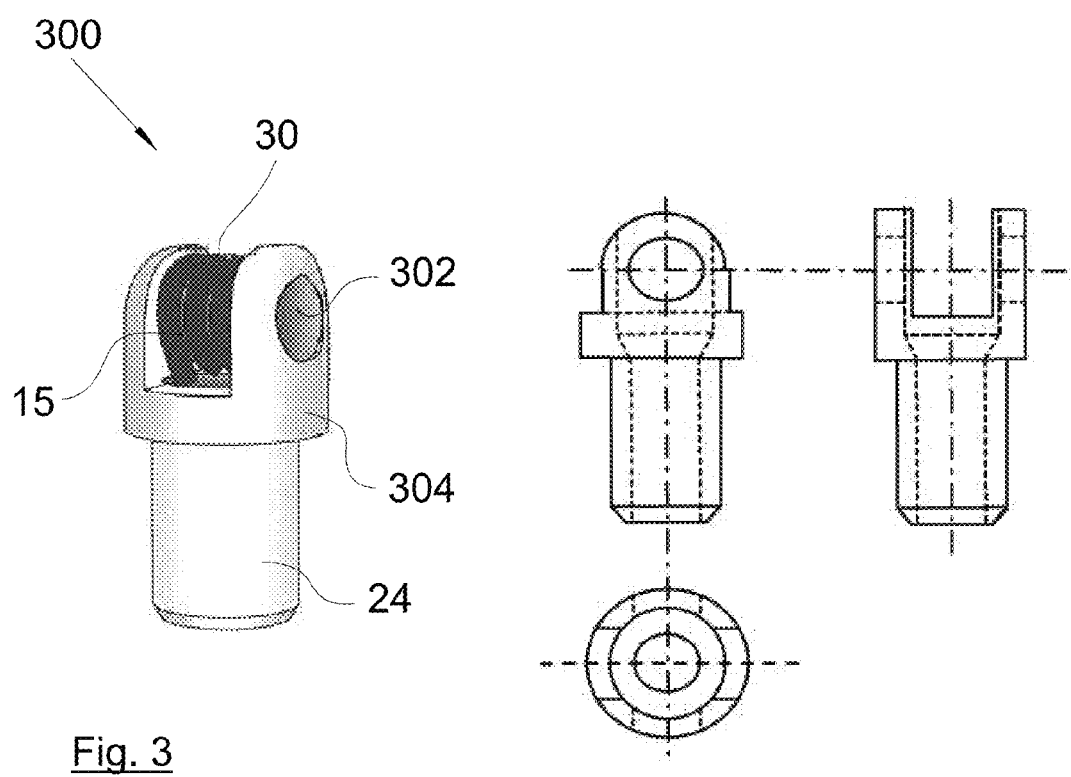

FIG. 3 shows a perspective view of a head 300, as well as a front view, a side view and a plan view. The head 300 carries the curved part 15 of the fibre and comprises means for applying a force from the curved part 15 onto the external medium S, then solid, such as a human tissue for example, at the contact area 30 and means for protecting the curved part 15 of the fibre against external mechanical stress, while guaranteeing a contact area (30, FIG. 4) between the external medium and the curved part 15 of the fibre.

Figure 4:
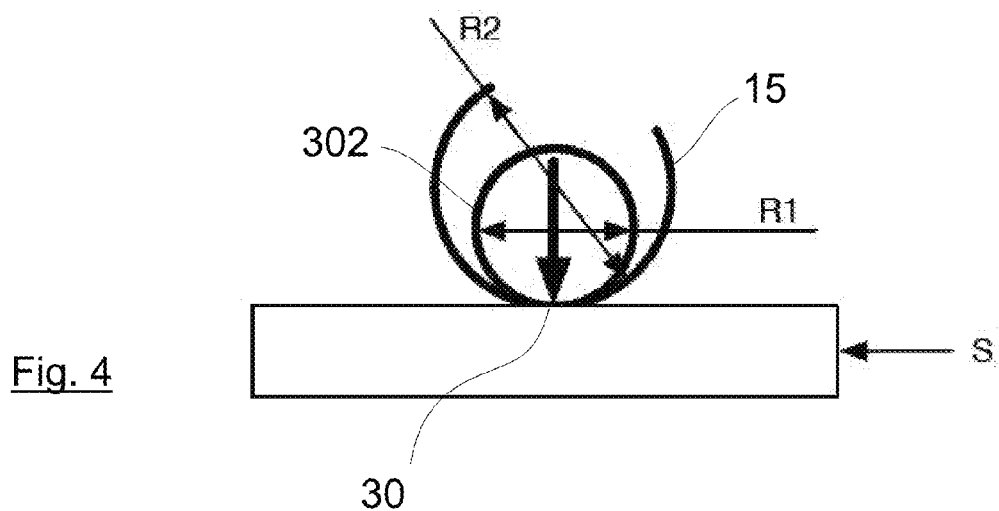
FIGS. 3 and 4 show a head according to a first embodiment of the invention for protecting the curved part of the fibre that is intended to be in contact with the external medium.

In the case of FIG. 3, the means for applying a force consist of a spindle 302. FIG. 4 shows the principle of applying the force. When an operator holds the sensor 100 by the protective sheath 24 and puts the curved part 15 of the fibre in contact on the external medium by exerting a slight pressure force, the spindle 302 transmits this force to the curved part 15 of the fibre, represented here by a vertical arrow. This curved part 15 of the fibre is then under pressure between the spindle 302 and the medium S, thus increasing the absorption of certain wavelengths of the flow circulating in the fibre by substances of this medium S, the evanescent-wave area being situated in a perimeter of a few microns outside the fibre.

Mechanical assemblies other than a spindle 302 may exist as long as these means make it possible to transmit the force exerted, by an operator, to the curved part 15 of the fibre, then in contact with the external medium S.

According to a particular embodiment, the curved part 15 of the fibre comprises a turn and the spindle 302 is slid inside this turn. The winding of the curved part 15 of the fibre in a turn increases the surface area of the fibre in contact with the external medium.

Preferably, the radius of curvature R1 of the spindle 302 is 10% less than the radius R2 of the turn and this radius of curvature R1 of the spindle 302 is designed to prevent any shearing of the fibre.

This embodiment is advantageous since it dispenses with the problems of differential expansion.

According to FIG. 3, the means for protecting the curved part 15 of the fibre are a clevis 304 with a through spindle 302. The spindle 302 extends through the clevis 304 and is slid inside the turn. Other forms of clevis with a through spindle may obviously be used. The clevis 304 may also comprise a part of a connector 20. The other part of this connector 20 then being secured for example to the sheath 24 in which the sections 11 and 12 of the fibre are housed.

The clevis 304 thus forms the head 22 for a sensor 100 and which can be connected to the sheath 24 removably so that this head 22 of the sensor 100 is replaced in the event of failure.

Figure 6:
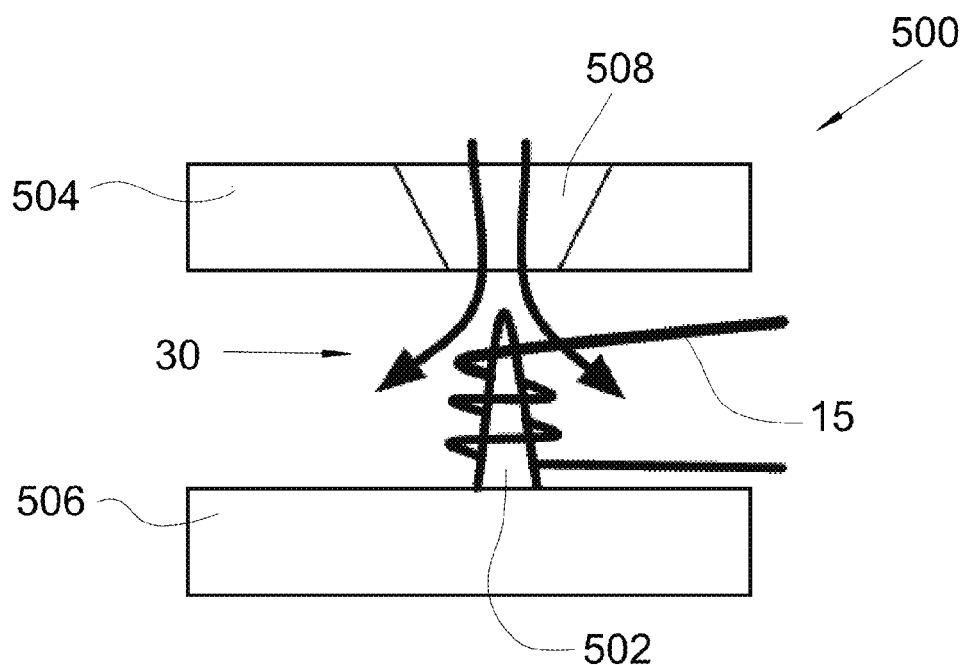
FIGS. 5 and 6 show a head according to another embodiment of the invention.
Figure 5:
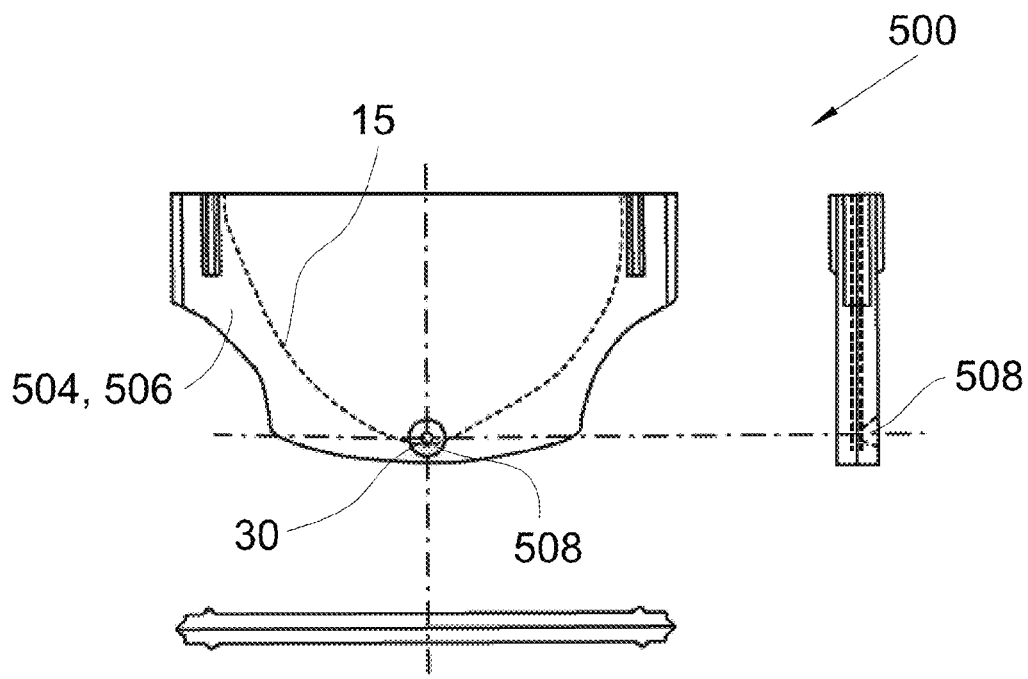

FIG. 5 shows the front, plan and side views of a head 500 according to the invention and FIG. 6 shows the principle of use of the head 500 in a flow of an external medium, then liquid.

This embodiment is particularly advantageous since the flow of the external medium over the curved part 15 of the fibre affords better impregnation of the fibre with the substances of this medium compared with what it normally is when the fibre is soaked in this medium.

The head 500 of the sensor 100 comprises means for providing contact of the curved part 15 of the fibre with the flow of the external medium.

The curved part 15 of the fibre comprises a turn wound around a stud 502 of the head 500 held in a fixed position with respect to the flow of the liquid. The winding of the curved part 15 of the fibre in a turn increases the surface area of the fibre in contact with the external medium.

Preferably, the radius of curvature R1 of the stud 502 is 10% less than the radius R2 of the turn and this radius of curvature R1 of the stud 502 is designed to prevent any shearing of the fibre.

This embodiment is advantageous since it dispenses with the problems of differential expansion.

The head 500 comprises means for protecting the curved part 15 of the fibre against external mechanical stresses, while guaranteeing a contact area 30 between the external medium and said curved part 15 of the fibre.

The means for protecting the curved part 15 of the fibre are represented here by two plates 504 and 506. The plate 504 comprises a flow conduit 508 that enables the liquid to flow between the two plates 504 and 506 (the two curved arrows represent this flow), and the other plate 506 comprises the stud 502. The two plates 504 and 506 are held in position with respect to each other so that the stud 502 is situated facing the opening of the flow conduit 508.

The plates 504 and 506 may have other forms than those shown here.

The plates 504 and 506 may also comprise a part of a connector 20. The other part of this connector then being secured to the protective sheath 24. Thus these plates 504 and 506 form a head 500 of the sensor 100 that may be removable.

The embodiments of the means for protecting the curved part of the fibre that is intended to be in contact with the external medium have been given here only by way of example and in no way limit the scope of the present invention. Any other variant embodiment of these means may be envisaged but also any other mechanical assemblies as long as these assemblies protect this curved part of the fibre against external mechanical stresses while guaranteeing a contact area between the external medium and said curved part of the fibre. In particular, when the external medium is gaseous, these means may be represented by a tube pierced with holes emerging on this curved fibre part.

FIG. 7 and FIG. 8 show the head 500 when it is positioned in line with the connector 20 and the protective sheath 24 in order to form the sensor 100 according to the invention. The means for fixing the head 500 are not shown and may take any suitable form. In this embodiment, the ends of the curved part 15 are disposed on the same face of the head 500.

Figure 10:
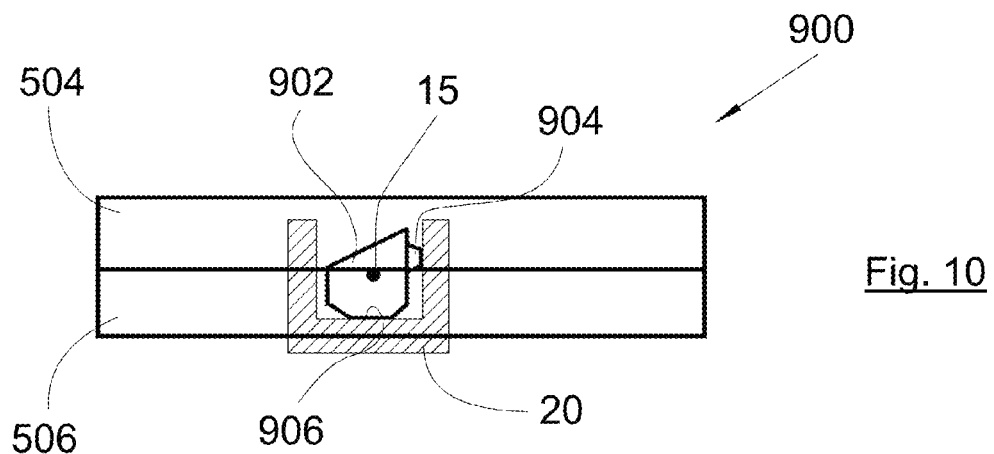
FIGS. 9 and 10 show the layout details of another head for a sensor according to the invention.
Figure 9:
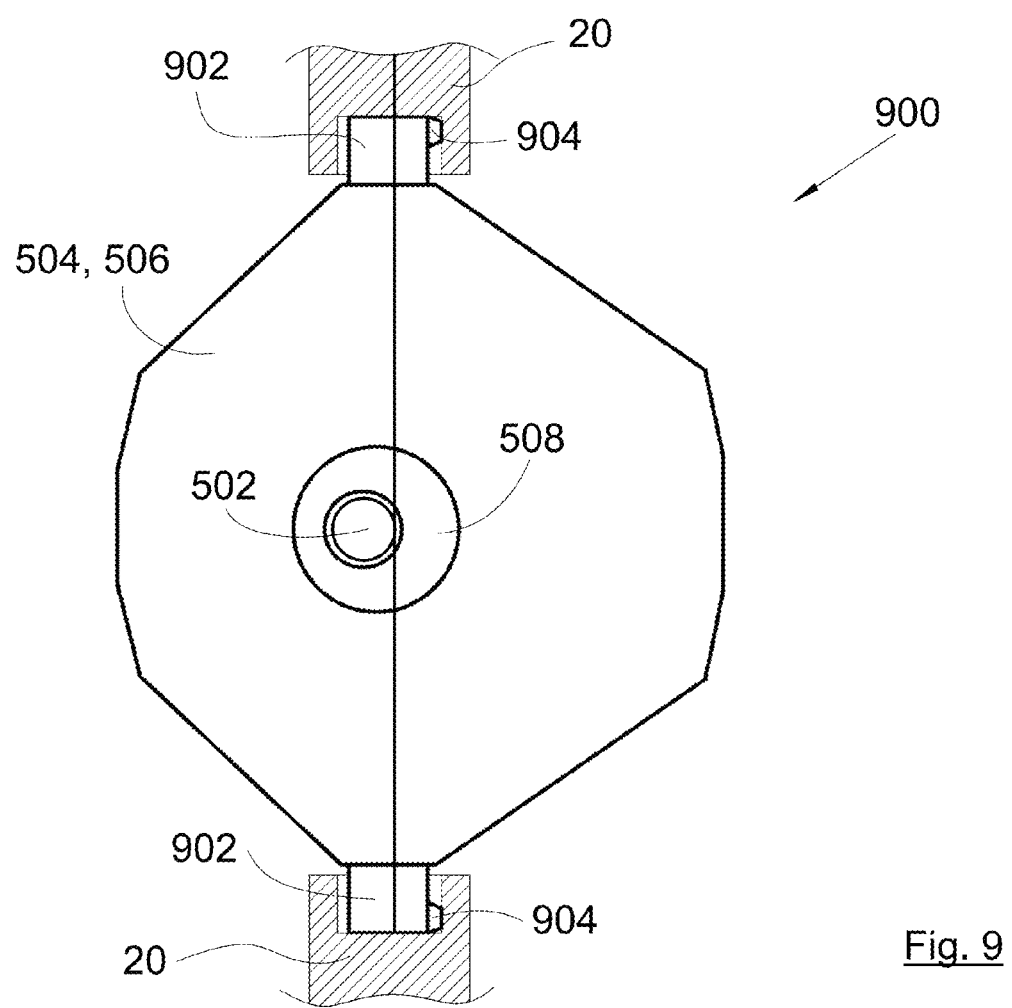

FIG. 9 and FIG. 10 show a head 900 according to another embodiment when it is positioned in line with the connector 20 and the protective sheath 24 in order to form the sensor 100 according to the invention. The means for fixing the head 900 are not shown and may take any suitable form. The head 900 also has a flow conduit 508 and a stud 502, but the ends of the curved part 15 are diametrically opposite.

Each end of the curved part 15 is housed in a shoe 702, 902 that consists of two protrusions, each issuing from one of the plates 504 and 506. The end of the curved part 15 is therefore placed between two protrusions, each issuing from one of the plates 504, 506. Each plate 504, 506 has two protrusions, each being designed to come opposite a protrusion on the other plate 506, 504, and between each pair of protrusions one end of the curved part 15 is housed.

The face of each shoe 702, 902 through which the end of the curved part 15 is accessible is able to be machined to produce a good contact surface and good propagation of infrared light at the junction with the corresponding section 11, 12.

In the case of FIGS. 7 and 8, the correct positioning of the ends of the curved part 15 with respect to the ends of the sections 11 and 12 is ensured by two ribs 704 that are produced on the external faces of the plates 504 and 506. The ribs 704 come into abutment on a wall of the connector 20 and can be machined to refine the positioning. It is therefore not necessary to machine the entire face of each plate 504, 506 but only the relevant ribs 704.

In the embodiment of the invention presented in FIGS. 7 and 8, there are two ribs 704 per plate 504, 506, but if only one plate, here the plate 506, is liable to be used for effecting the positioning with respect to the connector 20, only this plate 506 will carry ribs 704.

The correct positioning of the ends of the curved part 15 with respect to the ends of the sections 11 and 12 is also provided by a lateral rib 706 that is here produced by the junction of the two plates 504 and 506 and can also be machined to come into contact with another wall of the connector 20.

In general terms, at least one plate 504, 506 comprises ribs 704 and 706 machinable to form support surfaces in two different directions in order to suitably position the ends of the curved part 15 with respect to the ends of the sections 11 and 12.

The ribs 704 and 706 have support surfaces that are smaller compared with the surface of the plate 504, 506 from which they issue.

In the case of FIGS. 9 and 10, the correct positioning of the ends of the curved part 15 with respect to the ends of the sections 11 and 12 is provided by two ribs 904. Each rib 904 is produced on a face of each shoe 902 and the two faces are here coplanar. The ribs 904 come into abutment on a wall of the connector 20 and can be machined to refine the positioning.

The correct positioning of the ends of the curved part 15 with respect to the ends of the sections 11 and 12 is also provided by two planes 906. Each plane 906 is produced on a face of each shoe 902 and the two faces are here coplanar and perpendicular to the faces carrying the ribs 904. Each plane 906 can also be machined so as to come into contact with another wall of the connector 20.

In general terms, each shoe 902, that is to say each pair of protrusions, comprises a rib 904 and a plane 906 that can be machined so as to form support surfaces in two different directions in order to suitably position the ends of the curved part 15 with respect to the ends of the sections 11 and 12.

The ribs 904 and the planes 906 have support surfaces that are smaller compared with the surface of the plate 504, 506.

The invention claimed is:

1. Head (500, 900) for a sensor (100) comprising two sections of optical fibre (11, 12) for propagating infrared light at at least one infrared wavelength and generating evanescent waves to the outside in order to detect infrared signatures of an external medium, said head (500, 900) comprising:
   an optical fibre forming a curved part (15) intended to connect the two sections of fibre (11, 12) and to come into contact with the external medium in order to detect the infrared signatures interfering with the propagation of the evanescent waves propagating along the fibre, and
   means (504, 506) intended to protect the curved part (15) against external mechanical stresses, while guaranteeing a contact area (30) between the external medium and said curved part (15),
   wherein said means (504, 506) intended to protect the curved part (15) comprise a first plate (504) and a second plate (506) parallel to said first plate (504) and comprising a stud (502) with an axis which is perpendicular to said second plate (506), said first plate (504) comprising a flow conduit (508) intended to allow a flow of a liquid external medium between the plates (504, 506),
   wherein said curved part (15) is placed between said first plate (504) and said second plate (506),
   wherein said curved part (15) of the fibre comprises a turn wound around the stud (502), wherein each plate (504, 506) has two protrusions, each being designed to come opposite a protrusion on the other plate (506, 504), and in that one end of the curved part (15) is housed between each pair of protrusions.

2. Head (900) according to claim 1, characterized in that each pair of protrusions comprises a rib (904) and a plane (906) that can be machined so as to form support surfaces in two different directions.

3. Head (500) according to claim 1, characterized in that at least one plate (504, 506) comprises ribs (704, 706) that can be machined so as to form support surfaces in two different directions.

4. Head (500, 900) according to claim 1, characterized in that said stud (502) is situated facing an opening of the flow conduit (508).

5. Sensor (100) comprising:
   a protective sheath (24) enclosing two sections of optical fibre (11, 12) for propagating infrared light at at least one infrared wavelength and generating evanescent waves to the outside in order to detect infrared signatures of an external medium,
   a head (500, 900) according to claim 1, and
   a connector (20) fixing the head (500, 900) on the protective sheath (24).

6. Spectrometry system, characterized in that it comprises a sensor (100) according to claim 5.

* * * * *